US005693625A

United States Patent [19]
Barritault et al.

[11] Patent Number: 5,693,625
[45] Date of Patent: Dec. 2, 1997

[54] METHOD OF REGENERATING CELLS AND TISSUES USING FUNCTIONALIZED DEXTRANS

[75] Inventors: Denis Barritault, Paris; Jacqueline Jozefonvicz, Lamorlaye; Michele Tardieu, Champigny sur Marne; Faouzi Slaoui, Paris; Jean-Pierre Caruelle, Saint Maur; Jose Courty, Villecresnes, all of France

[73] Assignee: Therapeutiques Substitutives, Villetaneuse, France

[21] Appl. No.: 216,859

[22] Filed: Mar. 24, 1994

Related U.S. Application Data

[63] Continuation of Ser. No. 809,496, filed as PCT/FR90/00164, Mar. 9, 1990, abandoned.

[30] Foreign Application Priority Data

Mar. 9, 1989 [FR] France ................... 89 03086

[51] Int. Cl.$^6$ .................... A61K 31/715; C08B 37/02
[52] U.S. Cl. ............... 514/59; 514/2; 514/12; 514/54; 530/399; 536/51; 536/112
[58] Field of Search ............... 514/2, 12, 54, 514/59; 530/399; 536/51, 112

[56] References Cited

U.S. PATENT DOCUMENTS

| | | | |
|---|---|---|---|
| 2,997,423 | 8/1961 | Novak | 514/59 |
| 3,364,111 | 1/1968 | Morii et al. | 514/59 |
| 3,453,364 | 7/1969 | Magnus et al. | 514/59 |
| 4,180,567 | 12/1979 | Herb | 514/59 |
| 4,418,691 | 12/1983 | Yannas et al. | 424/548 |
| 4,613,502 | 9/1986 | Turkova et al. | 514/59 |
| 4,717,717 | 1/1988 | Finkenaur | 514/21 |
| 4,740,594 | 4/1988 | Mauzac et al. | 536/51 |
| 4,793,336 | 12/1988 | Wang | 514/59 |
| 4,883,755 | 11/1989 | Carabasi et al. | 435/240.2 |
| 4,902,782 | 2/1990 | Gospodarowicz et al. | 530/412 |
| 4,994,387 | 2/1991 | Levine et al. | 435/240.2 |
| 5,100,668 | 3/1992 | Edelman et al. | 536/51 |
| 5,120,715 | 6/1992 | Kato et al. | 514/54 |
| 5,132,223 | 7/1992 | Levine et al. | 435/240.2 |
| 5,155,214 | 10/1992 | Baird et al. | 530/399 |

FOREIGN PATENT DOCUMENTS 0267015  5/1988  European Pat. Off.

OTHER PUBLICATIONS

Heel et al; Drugs 18:89–102 (1979).
Sawyer et al; Surgery (Feb. 1979):201–204.
Plouët et al; Cell. Mol Biol. 30(2):105–110 (1984).
Tardieu et al; J. Biomat. Sci. Polymer Edn. 1(1):63–70 (1989).
Schaeker; Chemical Abstracts 69:1411w (1968).
Vasil'ev et al; Chemical Abstracts 77:105549d (1972).
Mincheva et al; Chemical Abstracts 94:202592w (1981).
Tardiell et al; Chemical Abstracts 113:204614q (Dec. 3, 1990).

*Primary Examiner*—Kathleen K. Fonda
*Attorney, Agent, or Firm*—Browdy and Neimark

[57] ABSTRACT

Compositions useful for regenerating cells and tissues comprise at least one functionalized dextran which has been substituted with carboxymethyl, benzylamide, or benzylamide sulfonate. These dextrans can be used alone or in combination with acid or basic fibroblast growth factors to enhance tissue or cell regeneration. Additionally, these dextrans enhance the stability of acid or basic fibroblast growth factors.

1 Claim, 3 Drawing Sheets

METHOD OF REGENERATING CELLS AND TISSUES USING FUNCTIONALIZED DEXTRANS

This application is a continuation of application Ser. No. 07/809,496, filed Dec. 13, 1991, now abandoned, which is the U.S. national stage entry of PCT/FR90/00164, filed Mar. 9, 1990.

FIELD OF THE INVENTION

The present invention relates to agents having a cell and tissue regenerating activity, consisting of dextrans, to stabilized compositions containing said agents in association with fibroblast growth factors (FGFs), and to their in vitro applications, such as the storage of FGFs and cell cultures, and in vivo applications as therapeutic agents, especially for healing and tissue regeneration, or as cosmetic agents.

BACKGROUND OF THE INVENTION

The existence of fibroblast growth factors (FGFs) has been demonstrated by numerous teams as a result of studying the biological activities of growth factors obtained from extracts of a very large number of tissues or organs (brain, pituitary gland, retina, vitreous humour, choroid, iris, cartilage, kidney, liver, placenta, corpus luteum, prostate gland, bone, muscle etc.).

The very diversity of the tissues studied and of the cells stimulated by these factors in vitro and in vivo, together with the large number of teams which have independently contributed to the characterization, isolation and complete identification of these factors, explains the multitude of names and initials used by these various authors to denote said factors.

It appears that all these extracts contain growth factors from the family of the FGFs and that this family can be divided into two main branches.

The first branch has been described under the names basic FGF, basic fibroblast growth factor or heparin binding growth factor II (HBGF II), brain-derived growth factor (BDGF), eye-derived growth factor II (EDGF II), astrocyte growth factor II (AGF II), cartilage-derived growth factor (CDGF) etc., while the second branch of the FGF family has been described under the names acid FGF or heparin binding growth factor I (HBGF I), brain-derived growth factor I (BDGF I) etc.

These factors have been named either according to the type of target cells used (fibroblast, astrocyte or endothelial cell growth factors with the initials FGF, AGF, ECGF), or according to the source from which this factor is extracted (for example growth factors derived from brain, retina or eyes, cartilage or hepatocytes in culture, with the respective initials BDGF, RDGF, EDGF, CDGF, HDGF), or else according to a biochemical or biological property (heparin binding growth factors (HBGF) or tumour angiogenic factor (TAF)); the two main branches of the family are named according to these initials, preceded or followed by acid or basic or by type I or type II.

It is by following the biological activity on cells in culture that these factors could be purified. The first physicochemical characteristics (molecular weight and isoelectric point) were published as early as 1975 (GOSPODAROWICZ, J. Biol. Chem., 250, 2515) for the basic form and in 1982 (BARRITAULT et al., J. Neurosci., 8, 477–490) for the acid form.

Purification of the two forms of FGF to homogeneity made it possible to establish their primary structures (ESCH et al., 1985, Proc. Natl. Acad. Sci. US, 82, 6507, for the basic form, and GIMENEZ G. et al., 1985, Science, 230, 1385–1388, for the acid form).

Isolation of the two forms was greatly favoured by the demonstration of a strong affinity of these factors for heparin and the subsequent use of affinity chromatography on immobilized heparin (SHING et al., 1984, Science, 223, 1296–1299).

It is known that, in vitro, FGFs are capable of stimulating the proliferation and differentiation of a large number of cells originating from different tissues and species.

There may be mentioned especially fibroblasts, endothelial cells, epithelial cells, keratinocytes, chondrocytes, myoblasts, astrocytes etc., and also neuronal survival.

It is also known that, in vivo, FGFs have neurotrophic, angiogenic and healing properties.

French patent 79 18282, which teaches a method of stimulating the growth of epidermal cells, may be cited especially; this method shows in particular the role of a partially purified aqueous retina extract, containing FGF, on the stimulation of said epidermal cells.

U.S. Pat. No. 4,477,435, which teaches a method of healing the corneal epithelium with the aid of a composition containing an aqueous retina extract, is also known.

Numerous studies are also known which involve demonstrating the existence of and characterizing FGFs and their role in the regeneration and healing of the skin, vessels, nerves, bones, muscles etc., both in vitro and in vivo.

There may be cited especially U.S. Pat. No. 4,444,760, which describes a brain-derived acid growth factor, its method of extraction and its application to the healing of wounds, and European patent application 186 084, which describes a method of stimulating the growth of vascular endothelial cells with the aid of a composition containing the brain-derived acid growth factor described above.

The FGFs described above are obtained by purification; FGFs obtained by genetic recombination are also known from international patent application PCT US86/01879.

Another healing composition based on at least one FGF is described in European patent application 243 179 and additionally comprises collagen and heparin and/or a glycoaminoglycan.

In these various documents, the topical application of FGF, by itself or in association, is effected with the aid of customary formulations such as creams, pastes, solutions and gels, or formulations associated with polymers, sponges and pumps permitting a slow release of the FGFs, as described in particular in international patent application PCT US86/01879, where it is specified that formulations comprising recombinant FGFs and appropriate excipients or carrier molecules can be prepared, especially lotions, gels, delayed-release forms or creams, said formulations being associated, if appropriate, with other active principles such as antibiotics. The delayed-release forms described in said patent application comprise polymers in particular.

The compositions obtained can be used especially as healing agents in the control of clotting, in the improvement of neurological damage and in the regeneration of hard tissues.

It is apparent, however, that FGF does not systematically stimulate healing; in fact, the absence of stimulation has been reported especially in J. Dermatol. Sing. Oncol.; the topical application of acid or basic FGF must therefore often be repeated in order to achieve the maximum effects, although some compositions of the prior art, such as FGF-impregnated polyvinyl alcohol sponges applied under the skin, induce the proliferation of fibroblasts and myoblasts.

This is due to thermal instability of the molecule, pH-related inactivation of the molecule, proteolysis by enzymes and interaction between the FGFs and the glycoaminoglycans, such as heparan sulphate or proteoheparan sulphate, of the cell membranes or basal membranes, leading to immobilization of the FGFs which can deny them access to the cell receptors.

Such disadvantages limit the possibilities of storing and using FGFs.

To mitigate this disadvantage, European patent application 267 015 has proposed a composition containing a polypeptide growth factor, more particularly EGF, and a sufficient amount of water-soluble polysaccharide to stabilize said factor against the loss of biological activity, especially in the presence of water. It is specified in said patent application that the water-soluble polysaccharides which can be used include cellulose derivatives, starch, agar, alginic acid, gum arabic, dextrans, fructans, inulin, mannans, xylans, arabinans, chitosans, glycogen and glucans.

SUMMARY OF THE INVENTION

Pursuing their studies on dextrans, the inventors have demonstrated novel properties of functionalized substituted dextrans; said dextrans are found to have an inherent cell and tissue regenerating activity and, in addition, they not only have a stabilizing action on an FGF composition but also cooperate with FGF in the biological activity of the latter.

The Applicant consequently set out to provide an agent having a cell and tissue regenerating activity and compositions containing said agent in association with FGFs, said compositions meeting the practical needs better than the compositions proposed in the prior art for serving the same purpose, especially in that the compositions according to the invention have a markedly improved stability, permitting easier storage and hence a superior therapeutic effect to that of the compositions of the prior art, and in that their frequency of application is thereby markedly reduced.

The present invention relates to an agent having a cell and tissue regenerating activity, characterized in that it consists of at least one functionalized substituted dextran.

In an advantageous embodiment of said agent, the functionalized substituted dextrans are selected from the group comprising soluble dextrans and insoluble dextrans.

Soluble functionalized substituted dextrans are understood as meaning those described especially in French patent n° 2 555 589 or in French patent n° 2 461 724.

Insoluble functionalized substituted dextrans are understood as meaning those described especially in French patent application n° 82 01641 or in French patent n° 2 461 724.

Such dextrans are stable and do not lose their properties with time.

Furthermore, they possess the unexpected property of having an inherent cell and tissue regenerating activity at low doses and, more particularly, a healing activity.

In an advantageous variant of this embodiment, said functionalized dextrans contain functions selected from the group consisting of carboxymethyl, benzylamide and benzylamidesulphonate.

The present invention further relates to a stabilized composition, characterized in that it comprises an agent having a cell and tissue regenerating activity, as defined above, in association with at least one acid FGF and/or one basic FGF and/or one derivative and/or one analogue and/or one fragment thereof having a biological activity, which agent is capable of partially or totally restoring the biological activity of the acid and/or basic FGF/FGFs inactivated by prolonged storage or temperature.

Such a composition has a cell and tissue regenerating activity, and especially a healing action, which is superior to that of the compositions of the prior art.

In an advantageous embodiment of the composition according to the invention, said composition comprises from 0.1 to 1000 µg/ml of at least one agent having a cell and tissue regenerating activity, as defined above, and from 0.01 ng to 300 µg of at least one FGF selected from the group consisting of acid FGFs, basic FGFs and their derivatives, their analogues and their fragments having a biological activity.

According to the invention, the stabilized compositions containing the agent having a cell and tissue regenerating activity, by itself or in association with at least one FGF, can be associated with other active principles and/or at least one pharmaceutically acceptable vehicle and/or a physiologically acceptable support.

The associated active principles are selected from the group comprising especially local anaesthetics, antiinfectious agents, serum proteins and collagen.

Lidocaine may be mentioned in particular as a local anaesthetic and sodium salts, silver salts, derivatives thereof or sulphadiazines may be mentioned in particular as bacteriostatic substances. Streptomycin may be mentioned as an antibiotic; serum albumin or fibronectin may be mentioned as serum proteins; soluble collagens and elastin may also be mentioned.

According to the invention, if the vehicle is water, said composition is also associated with buffers and/or appropriate salts so as to keep the mixture approximately at a pH of between 6.8 and 7.4 and at an ionic strength of between 0.1 and 0.2, for example, in NaCl equivalents.

Such associations according to the invention are hereafter referred to as "matrix compositions".

In one advantageous embodiment of said composition, the latter is associated with liposomes.

Such compositions according to the invention are hereafter referred to as FGF/functionalized dextran/liposome compositions and functionalized dextran/liposome compositions.

In another advantageous embodiment of said composition, the support is selected from the group comprising especially dressings and biomaterials.

In another embodiment of the composition according to the invention, the latter is in the form of an aerosol if the vehicle is an appropriate gas.

The "matrix" composition is advantageously applied directly in solution or as an aerosol.

According to the invention, said composition, especially said "matrix" composition, is included in a medicinal form such as an ointment, cream, paste or lotion, or impregnated in a gel, especially a collagen gel.

Also according to the invention, said composition, especially said "matrix" composition, is included and/or impregnated in an appropriate support, such as a dressing or biomaterial, which directly or indirectly favours cell repair (for example a surgical suture thread or coral for a bone graft).

Said "matrix" composition can be included especially in traditionally used creams or lotions, in particular lanolinbased creams such as "SILVEADENE", "MARIO", "AQUAPHOR" and "EQUALIA", for application to the skin; it can also be included or impregnated in dressings such as those made of textiles, synthetic fabrics or sponges, or natural products used for covering wounds, for example collagen gels or dermis of animal origin.

Said "matrix" composition according to the invention must impregnate these various forms of dressings so that the FGF and/or the substituted functionalized dextran can be in contact with or diffuse as far as the target tissues.

The composition according to the invention is kept especially on the site of the injury and on open injuries so as to maintain hydration in accordance with the techniques of those skilled in the art, which are particularly developed in the field of skin grafts.

Occlusive dressings can be impregnated in the same manner, or adsorbed, or they can cover a natural or synthetic support.

For applications to the cornea, the vehicle must be compatible with the eye's tolerance (for example the product marketed under the name "LACRIBULE", saline solutions or isotonic solutions, for example "NEOCADRON" (Merck-Sharp-Dohme)).

These vehicles can also contain preservatives such as benzyldimethylalkylammonium chlorides or sodium ethylenediaminetetraacetate (EDTA).

According to the invention, the FGF/functionalized dextran/liposome composition or the functionalized dextran/liposome composition is included in a medicinal form such as an ointment, cream, paste or lotion, or impregnated in a gel, especially a collagen gel.

In the case of insoluble functionalized dextrans, these can also be included, by themselves or in association with FGF, in carriers such as creams, gelatins or collagen gels, or on synthetic or natural fibres, which are the usual supports for cover dressings. The insoluble functionalized polymers can be included by the addition of collagen solution and gelling. The procedures described in a series of patents in the name of YANNAS can be used. In these patents (U.S. Pat. No. 4,060,081), a composite laminar composition gives an equivalent skin in which the part in contact with the injury is covered with collagen crosslinked with a glycosaminoglycan, the mixture being obtained by adding glycosaminoglycans to the solubilized collagen and the whole being precipitated or crosslinked with glutaraldehyde (U.S. Pat. No. 4,418,691).

The composition according to the invention is prepared especially by mixing at least one appropriate FGF with at least one agent having a regenerating and stabilizing activity.

Said FGFs are obtained by extraction and purification from natural sources, by chemical synthesis or else by appropriate genetic recombination techniques.

Said FGFs are of human origin or else originate from other animals, especially other mammals.

Numerous purification methods for extracting and isolating the two forms of FGF from these natural sources (retina, brain, pituitary gland, placenta, kidney etc.) have been described in the prior art.

The preferred methods of the present invention are those described in Biochimie, 1986 (COURTY et al.), or that described in French patent application 2 613 936, which utilizes affinity chromatography on biospecific substituted polystyrenes.

These preferred methods include a step for treating the tissue extract at very acid pH, thereby excluding any risk of viral contamination, and the use of chromatography on immobilized heparin or substituted polystyrene.

The two forms of FGF can thus be isolated and separated, with the other proteins or individually, with a sufficient degree of purity to be devoid of significant amounts of other contaminating materials.

DETAILED DESCRIPTION OF THE INVENTION

Figure 1:
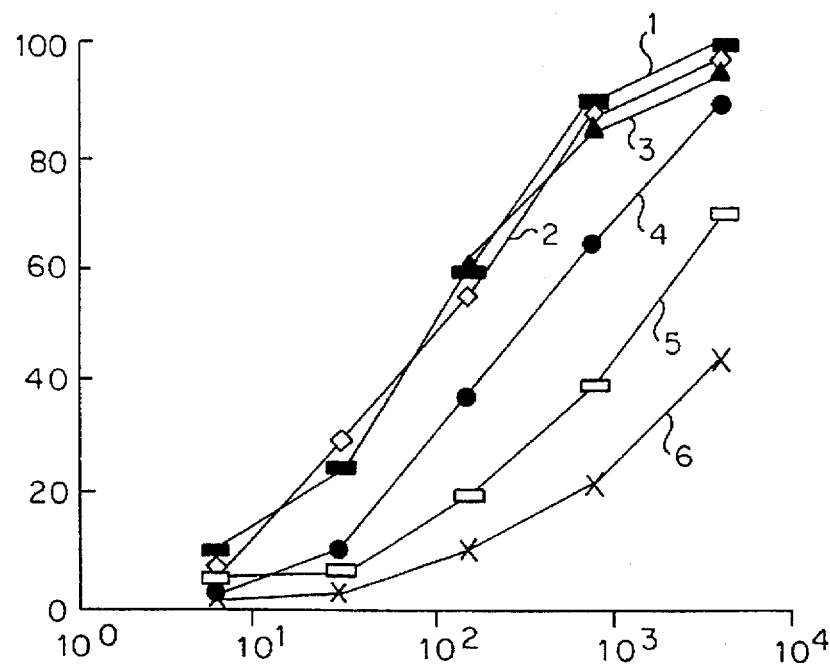
FIG. 1 shows the dose-response curve of bFGF on CCL38 fibroblasts.

Apart from the foregoing provisions, the invention also includes other provisions, which will become apparent from the following description referring to Examples of how to carry out the method forming the subject of the present invention and to Examples showing the effect of functionalized substituted dextrans on the protection of the biological activity of FGFs.

It must be clearly understood, however, that these Examples are given solely to illustrate the subject of the invention without in any way implying a limitation.

EXAMPLES

Example 1

Method of stabilizing FGFs

1) Preparation of a Functionalized Substituted Dextran (Cell and Tissue Regenerating Agent)

30 grams of dextran T40 (0.185 mol) are dissolved in 146 ml of distilled water and cooled to 4° C. in a bath of melting ice. 59.2 g of NaOH (1.48 mol) are dissolved in 100 ml of distilled water and then cooled to 4° C. The sodium hydroxide solution is poured slowly into the dextran solution, with stirring, and the whole is kept at 4° C. for 20 minutes. 61 g of $ClCH_2COOH$ (0.647 mol) are then added very gradually so that the temperature reaches 20° C. after 5 minutes. The reaction medium is then heated to 40° C. over 10 minutes, kept at this temperature for 90 minutes and then cooled to about 20° C. The pH is lowered to about 7 with concentrated acetic acid. The whole is precipitated in 2 litres of methanol, filtered off, washed twice with 1 litre of ethanol and then dried under vacuum at 40° C.

10 g of the above modified polymer are dissolved in 55 ml of distilled water acidified to pH 3. 60 ml of dimethylformamide are added very gradually, with stirring, the pH being kept at a value of 3. The temperature is lowered to −15° C. and 12.3 ml of N-methylmorpholine are added with 14.5 ml of isobutyl chloroformate. This is followed by the addition of 12.2 ml of benzylamine. After 30 minutes, the polymer is precipitated in 800 ml of methanol, filtered off and dried.

9 g of the above modified polymer are dispersed in 25 ml of anhydrous methylene chloride. A mixture of 0.26 ml of HSO₃Cl and 2.5 ml of methylene chloride is introduced into the reactor and the whole is kept at room temperature for 4 hours. After filtration and washing with methylene chloride, the product is dried and dissolved in 30 ml of water and the pH is adjusted to a value of 7.0. The solution is ultrafiltered against a buffer solution and then against distilled water. The solution is then lyophilized until the dry polymer is obtained.

Another method of preparing a functionalized substituted dextran can be used, such as that described in European patent n° 0 023 854.

2) Preparation of the FGF/FGFs

The cell extract/extracts are treated overnight in the presence of acetic acid at pH 3 and the FGFs are then separated out by chromatography on immobilized heparin or substituted polystyrene.

3) Preparation of a Stable FGF Composition According to the Invention

A solution of dextran is prepared from the dry polymer obtained in 1) by dissolving it in an isotonic phosphate buffer (PBS) to give a concentration of 400 µg/ml.

The FGFs extracted in 2) are dissolved in this buffer, containing the appropriate substituted dextrans, so as to give an FGF concentration of 100 µg/ml.

Example 2

Stabilized Ointment According to the Invention

| FGF | 10 µg |
| FD | 5 mg |
| Carboxymethyl cellulose | 2.5 g |
| Apyrogenic sterile purified water | 100 ml |

FD=type E functionalized dextran as defined in Table III below.

The cream obtained can be applied for three days to a scarification-type wound on a rat.

Example 3

Stabilized Dressing According to the Invention

The support for the dressing consists of a "Pangil" collagen film from Laboratoires FOURNIER, impregnated by passive adsorption with a mixture of FGF and functionalized dextran in the following proportions:

| FGF | 10 µg |
| FD | 500 µg |
| Isotonic solution | 10 ml |

After incubation of the collagen film for 30 minutes at 4° C. in the solution described above, a dressing is obtained which can be used in cases of ulcerations of various kinds and superficial or deep wounds.

This dressing can be stored under vacuum and packed.
Study of the Effect of Functionalized Biospecific Polymers on the Protection of the Biological Activity of FGFs In Vitro Methodology Used for Measurement of the Biological Activity of FGFs In Vitro The methods of evaluating the biological activity of FGFs in vitro are described in numerous publications and are all based either on measurement of the increase in the number of cells induced by increasing doses of factors added to the cell culture medium, or on an increase in the incorporation of tritiated thymidine into the DNA of cells stimulated by the growth factor. In the two methods referred to, these increases are dependent on the dose of factor added and it is therefore possible to establish dose effects and dose-response curves with a maximum stimulating effect. By way of simplification, one unit of stimulation is defined as the dose of growth factor which, when added to one millilitre of culture medium on target cells, is capable of inducing an increase in the number of cells or in the incorporation of tritiated thymidine which corresponds to half (50%) of the maximum value of this increase measured in the dose-response curve. This definition and the reproducibility of these measurements are explained especially in PLOUET et al., 1984, Cellular and Molecular Biology, 30, p. 105.

Example A

Protective Effect of Substituted Dextran Against the Inactivation of Acid and Basic FGFs by Acid and Alkaline pH Value In these experiments, the FGFs are in solution at a concentration of 100 µg per millilitre in an isotonic phosphate buffer (PBS) containing no dextran (control) or containing substituted dextran at 400 µg/ml. 10 µl of these various solutions are taken and mixed with 1 ml of either PBS, or dilute acetic acid (CH₃COOH) adjusted to pH 2 (about 1N), or dilute sodium hydroxide (NaOH) adjusted to pH 9.0. These samples are incubated at 20° C. for two hours and 1 µl is taken for determination of the biological activity.

FIG. 1 shows the dose-response curve of bFGF on CCL39 fibroblasts.

In this Figure, the logarithm of the bFGF concentration in pg/ml is plotted on the abscissa and the percentage stimulation on the ordinate.

Curve 1 corresponds to the control; curve 2 corresponds to bFGF by itself at pH 2; curve 3 corresponds to bFGF in the presence of dextran at pH 2; curve 4 corresponds to bFGF in the presence of dextran at pH 9; curve 5 corresponds to bFGF by itself at pH 9; and curve 6 corresponds to the control in the presence of dextran.

The increase in the incorporation of tritiated thymidine represents the value of the number of counts per minute (cpm) obtained at the plateau of the dose-response curve of bFGF by itself minus the value in cpm for tritiated thymidine incorporated into the cells in the absence of FGF and determined in the same experiment.

Curves 3 and 4 show that bFGF in the presence of dextran preserves its stimulating power in both acid and basic media.

Table I summarizes the results obtained with acid and basic FGFs. The unit of stimulation is arbitrarily fixed at 1 for the starting aFGF or bFGF incubated for two hours at 20° C.

TABLE I

| | pH 2 | pH 7 | pH 9 |
|---|---|---|---|
| FGFb (0° C.) | | 0.9 | |
| FGFb (2 h, 20° C.) | 53 | 1 | 13 |
| FGFb + FD (2 h, 20°) | 1 | 1 | 2.5 |
| FGFb + HS (2 h, 20°) | 3 | 1 | 4 |
| FGFa (0°) | | 1 | |
| FGFa (2 h, 20°) | 6 | 1 | 6 |
| FGFa + FD (2 h, 20°) | 0.5 | 0.4 | 2 |
| FGFa + HS (2 h, 20°) | 1.5 | 0.8 | 4.5 |

FD = functionalized dextran, which in this Example is dextran E as defined in Table III below.
HS = heparan sulphate (from BIOVALORIS in Plouhermel (Ile-et-Villaine, FRANCE)).

This Table shows the protective effect of FD (functionalized dextran) against the inactivation of acid and basic FGFs induced by acid and alkaline pH values.

The incubation of basic FGF for two hours at 20° C. in a buffer solution of pH 2 to 9 induces inactivation of the biological activity of the basic FGF.

In fact, 53 times more product are needed at acid pH and 13 times more at basic pH in order to induce a biological effect in the initial product.

The addition of FD to this mixture totally protects the biological activity of the basic FGF against incubation at pH 2 or 9.

Similar results are observed in the case of acid FGF as far as the two types of treatment are concerned.

Example B

Effect of Functionalized Dextran (FD) on the Inactivation of FGFs by Temperature in the Short and Long Term In this Example, FGF prepared as in Example A is incubated at 40° C., 20° C., 37° C. or 60° C. for different times in the absence or presence of 400 µg of functionalized dextran (FD), as defined in Table III below, and then determined.

The results are given in Table II below.

TABLE II

|  | 4° C. | 20° C. | 37° C. | 60° C. |
|---|---|---|---|---|
| bFGF t = 0' | 1 | | | |
| bFGF t = 30' | 1 | 1 | 3.5 | >100 |
| bFGF + FD t = 30' | 1 | 1 | 1 | 9 |
| aFGF t = 0' | 1 | | | |
| aFGF t = 30' | 1 | 1 | 2 | >100 |
| aFGF +FD t = 30' | 0.4 | 0.4 | 0.4 | 5 |
| bFGF t = 24 h | 1 | 1 | 6 | |
| bFGF + FD t = 24 h | 1 | 1 | 1 | |
| aFGF | 1 | 1 | 1 | |
| aFGF + FD | 0.4 | 0.4 | 0.4 | |
| bFGF t = 7 days | 2 | 5 | >100 | |
| bFGF + FD t = 7 days | 1 | 1 | 1 | |
| bFGF + HS t = 7 days | 1 | 2 | 6 | |
| aFGF t = 7 days | 2.5 | 8 | >100 | |
| aFGF + FD t = 7 days | 0.4 | 0.4 | 3 | |

FD = functionalized dextran
HS = heparan sulphate

The initial unit of stimulation is arbitrarily fixed at a value of 1.

This Table shows a strong inhibition of the activation of acid or basic FGF induced by treatment for one week at 37° C. The presence of FD in the incubation medium protects both types of FGF against thermal denaturation.

Similar results are observed using HS (heparin sulphate), the biological equivalent of FD.

Example C

Effect of Different Functionalized Dextrans on the Dose-Response Effects of FGF

The effect of different functionalized dextrans is measured as a ratio in Table III below.

TABLE III

| Dextran derivative | % D | % W | % X | % Y | R/us |
|---|---|---|---|---|---|
| A | 100 | 0 | 0 | 0 | 1 |
| B | 0 | 106 | 0 | 0 | 1.6 |
| c | 0 | 84 | 21 | 0 | 1.7 |
| D | 10 | 76 | 0 | 14 | 2.6 |
| E | 0 | 89 | 6 | 5 | 2.36 |
| F | 0 | 74 | 16 | 10 | 3.1 |
| G | 65 | 30 | 1 | 4 | 2.54 |
| H | 29 | 42 | 24 | 5 | 2.1 |

Percentages:
D : dextran
W : carboxymethyl
X : benzylamide
Y : benzylamidesulphonate R/us is the value of the ratio of the values of the units of stimulation of aFGF without functionalized dextran divided by the unit of stimulation in the presence of functionalized dextran.

Study of the Effect of Functionalized Biospecific Polymers on the Protection of the Biological Activity of FGFs In Vivo Example D Kinetic, Planimetric and Histological Studies of the Healing Effect of the Association FGF/Functionalized Dextran Experimental Protocol The operations are carried out on male Wistar rats weighing 300 to 400 grams. Each experiment is performed on a group of 5 animals.

Types of Wounds

Two types of skin wounds are made on the pre-shaven dorsum of the animals.

Skin removals are carried out with a punch (0.6 cm in diameter) down to the muscle floor.

Scarifications of 1 cm in length are made with a scalpel. They do not affect the dermo-epidermal region.

Procedure

According to the type of wound, the injuries are treated with different mixtures of products dissolved in sterilized buffered isotonic solution (pH 7.4).

In the case of the punch wounds, these solutions are deposited in a collagen plug (GINGESTAT) pre-cut to the exact measurements of the tissue excision.

In the case of the scarifications, the products are deposited directly in liquid form on the wound.

The effects of the association of FGF (basic, acidic or a mixture in a solution of 1 ng to 10 µg/ml) and functionalized dextrans (in a solution of 100 ng to 1 mg/ml) are evaluated and compared with the action of a substituted functionalized dextran by itself and of each of the constituents considered as reaction controls (collagen, dissolving solution, FGF).

Each experimental group of animals is sacrificed after an interval of time defined by 24-hour periods and the injured regions are removed for two types of study:

an external morphological analysis with planimetry of the wound;

a histological study.

Results

I—Stabilizing Effects of Functionalized Dextrans

FGF radiolabelled with $^{125}I$ is deposited in a collagen plug in the presence or absence of functionalized dextran.

The variation in the radioactivity in the impregnated collagen is assessed as a function of time.

Figure 2:
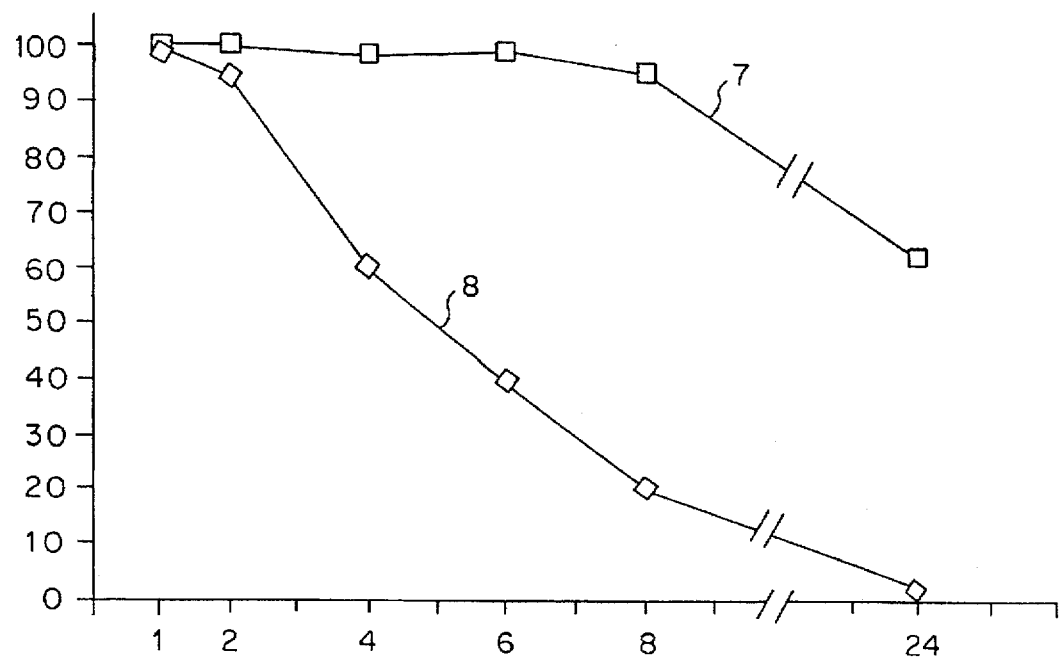
FIG. 2 shows the results of studies of the healing effect of FGF/functionalized dextran.

The results are illustrated in FIG. 2, in which the time in hours is plotted on the abscissa and the percentage radioactivity on the ordinate. Curve 7 corresponds to FGF in the presence of dextran and curve 8 corresponds to FGF by itself.

The radioactivity is measured in the collagen gel and in skin removed at the periphery of the wound, 2 cm from the latter, by a punch equivalent to the one originally used.

II—Morphological and Histological Studies

A) Morphological Study

Observation of the change in the wounds with the naked eye makes it possible to establish a very distinct action of the association FGF+functionalized dextran on the rate and quality of the superficial healing (epidermization+lysis of the clot).

1) After 24 hours, the collagen plugs impregnated with this association have totally adhered to the walls of the wound and can only be removed by lesion of the regenerated tissues. The control experiments only show total adhesion of the collagen plugs after 36 to 48 hours.

2) Re-epithelialization is visible to the naked eye after the third day when the association FGF+functionalized dextran is present, whereas an identical picture for the controls requires experimental periods of 5 to 7 days.

3) Planimetric analysis: Planimetric analysis of the external surface of the wounds shows the total absence of retraction of the regenerating tissues.

The degree of scar retraction is evaluated as a function of time by considering the ratio P/A, where P is the perimeter of the wound and A the area of the scar.

The order of magnitude of this ratio P/A is of the type K/R, where K is a constant and R the radius of the original circular wound.

As a function of time, the lower and more constant this ratio, the more the scar retains a planimetry similar to that of the original lesion. Consequently, the lower the ratio P/A, the more limited is the degree of scar restructuring. The healing quality can thus be reflected by the absence of contraction.

Figure 3:
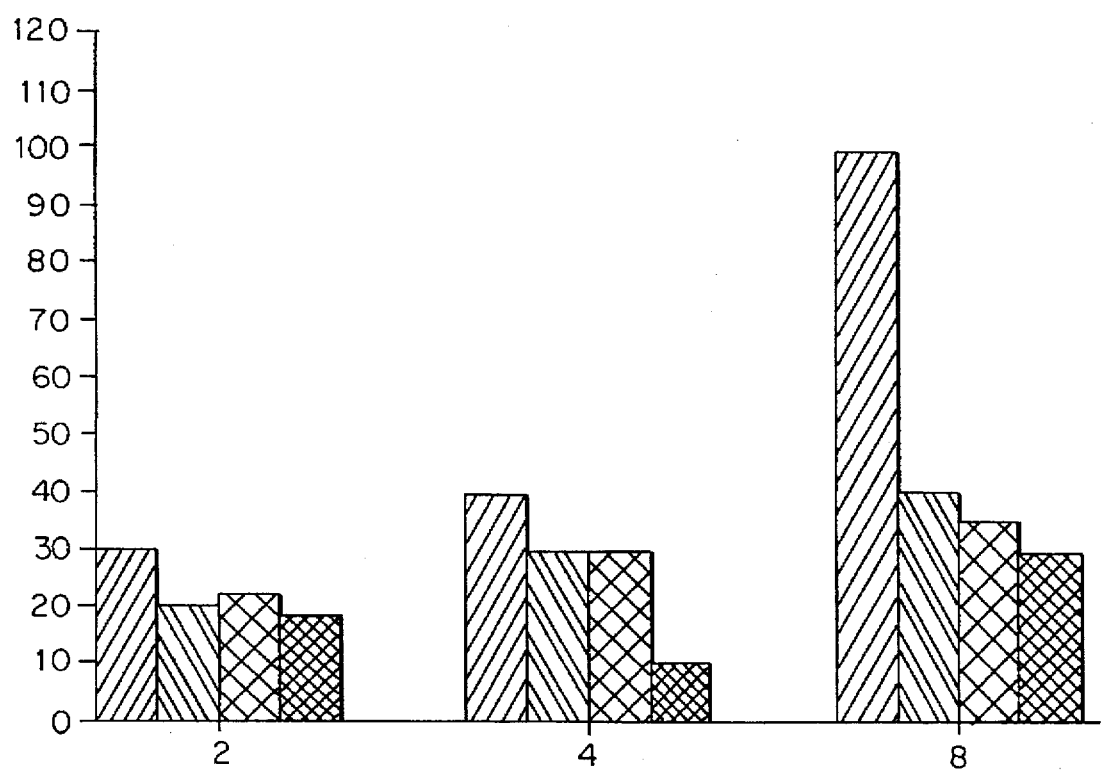
FIG. 3 shows the results of morphological studies on changes of wounds using FGF/functionalized dextran.

The results obtained are illustrated in FIG. 3, in which the time in days is plotted on the abscissa and the ratio P/A on the ordinate. The degree of retraction is represented by ■ for the control, by ■ for bFGF, by ⊠ for FGFs in the presence of heparan sulphate and by ▨ for FGFs associated with functionalized dextrans.

The results are also shown in Tables IV and V below; Table IV gives the percentage healing area as a function of the amount of functionalized dextran (FD) in the presence or absence of bFGF; Table V gives the ratio P/A under the same conditions.

TABLE IV

| P/A | CONTROL | FD 500 µg | FD 50 µg | FD 5 µg | bFGF 1 µg | bFGF 1µg + FD at different concentrations: | | |
|---|---|---|---|---|---|---|---|---|
| | | | | | | 500 µg | 50 µg | 5 µg |
| 2 d | 0.17 | 0.20 | 0.13 | 0.08 | 0.13 | 0.19 | 0.09 | 0.10 |
| 4 d | 0.20 | 0.18 | 0.19 | 0.11 | 0.15 | 0.13 | 0.11 | 0.08 |
| 8 d | 0.58 | 0.41 | 0.30 | 0.28 | 0.24 | 0.38 | 0.21 | 0.19 |

TABLE V

| | FD 500 µg | FD 50 µg | FD 5 µg | bFGF 1 µg | bFGF 1 µg + FD at different concentrations: | | |
|---|---|---|---|---|---|---|---|
| | | | | | 500 µg | 50 µg | 5 µg |
| 2 d | 125 | 104 | 173 | 147 | 112 | 160 | 128 |
| 4 d | 105 | 213 | 160 | 169 | 182 | 231 | 260 |
| 8 d | 280 | 128 | 145 | 386 | 329 | 237 | 253 |

The effects of functionalized dextrans on this retraction are particularly visible on the fourth and eighth days after the operation.

The Tables above clearly show the inherent healing effect of dextrans; in fact, in Table IV, the percentage area in the presence of 5 µg of FD after 8 days is similar to that in the presence of 1 µg of bFGF by itself, these percentages themselves being less than the control.

The retraction is very small in comparison with those observed in the control experiments or those observed in the presence of FGFs by themselves or associated with heparan sulphates, these conditions already being distinctly more favourable than those of the control.

B) Histological Study

The treated regions are removed, fixed and impregnated with paraffin. The histological study is carried out on 7 µm sections. The stains used permit topographical and histochemical studies.

The histological analysis shows that the association FGF+FD accelerates the traditional steps of dermo-epidermal healing and enhances the quality of the reconstituted tissues.

Impregnated collagen permits a very rapid colonization (1 day) of the surrounding categories of cells (fibroblasts, smooth muscle cells) from the healthy surrounding tissues and in particular from the connective tissue of the subjacent striated muscle floor.

At the same time, neoangiogenesis enables the tissue which is being formed to be colonized by a very high density of blood capillaries. After three days (as opposed to five to six for the controls), the re-epithelialization which had started from the epidermis of the lips of the wound joins up the edges. On the fourth day, the epidermis is totally reconstituted and the subjacent tissues, which are totally reorganized, have a normal density compared with the controls, for which the density is much lower. These same illustrations reveal the absence of retraction of the edges of the wound in the case of the punch wounds treated with the association FGF+functionalized dextrans, in contrast to the controls, where the excised tissues are made up by extraction.

Figure 4:
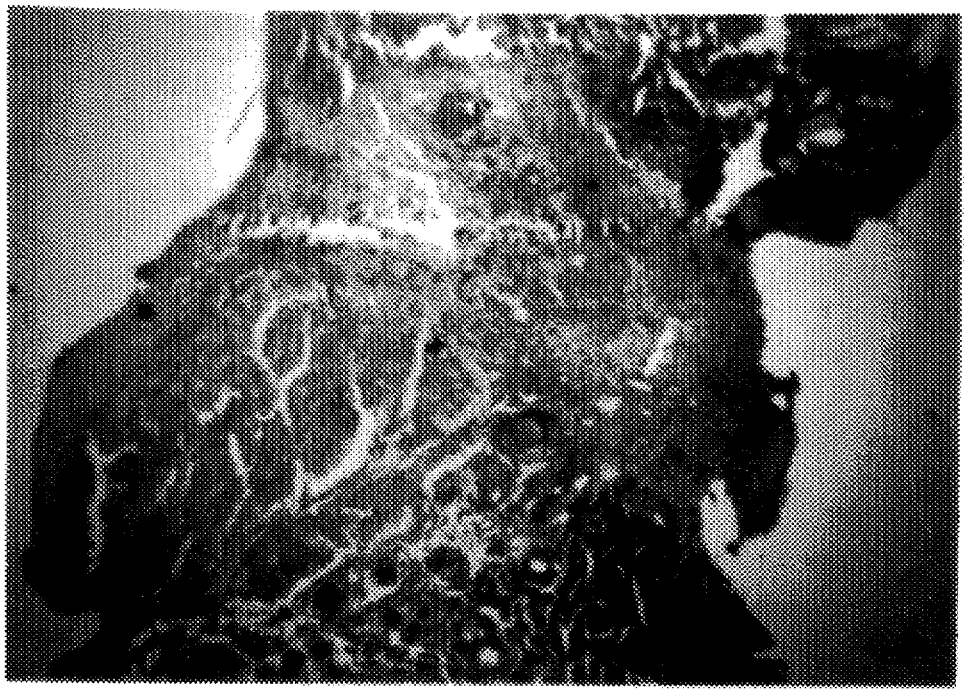
FIG. 4 shows a photograph of a histological section of a control scar four days after the wound was made.
Figure 5:
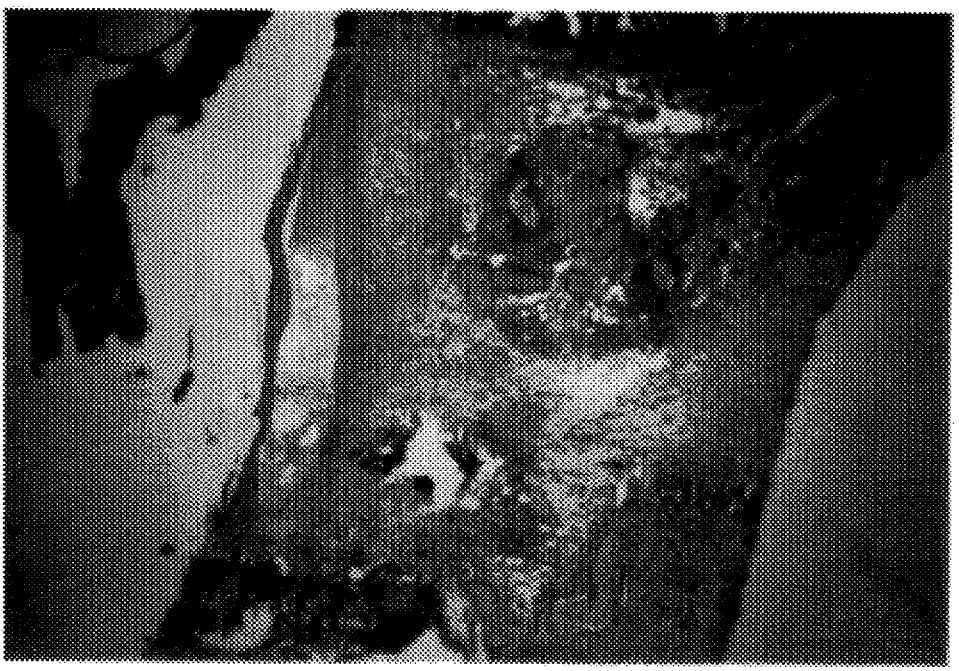
FIG. 5 shows a photograph of a histological section of a scar after treatment with a collagen plug impregnated with a solution of bFGF and 1 µg/ml functionalized dextran at 50 µg/ml four days after the wound was made.

The effects of the association of bFGFs and functionalized dextrans on the healing quality, compared with natural healing without the addition of products, are shown in FIGS. 4 and 5.

FIG. 4 shows a photograph of a histological section of a control scar (absence of treatment) four days after the wound was made (X 40). FIG. 5 shows a photograph of a histological section of a scar after treatment with a collagen plug impregnated with a solution of bFGF and 1 µg/ml and functionalized dextrans at 50 µg/ml, four days after the wound was made and at the same magnification of 40.

FIG. 5 shows the epidermis (E) entirely re-constituted, whereas in FIG. 4 it is not reformed. A retraction of the surrounding tissues on the control wound is not recorded on the treated wound. This cicatricial space, which is relatively anarchic in FIG. 4, has organization and a satisfactory cell density in the case of the treated wound (FIG. 5). It is characterized by the presence of blood vessels representing the local angiogenic effect of the association of the products of this invention.

It is therefore apparent that the association bFGF+functionalized dextran is a powerful healing agent in vivo, which on the one hand accelerates the natural regenerative processes and on the other hand permits an enhanced healing quality through the absence of any retraction phenomenon such as the rapid mobilization of the different categories of cells necessary for tissue restoration.

Example E

Planimetric and Histological Studies of the Healing Effect of Functionalized Dextrans The experimental protocol, which is identical in every respect to that employed in the context of Example D, is carried but in order to assess the healing effects of functionalized dextrans. The dextrans studied are listed in Table III of Example C. The healing effects of these functionalized dextrans or of their association were assessed relative to two control experiments in the presence of vehicle by itself, a collagen plug or a collagen plug impregnated with unsubstituted dextran (product designated by A).

A—Morphological Study

Observation of the change in the wounds with the naked eye makes it possible to establish a very distinct action of functionalized dextrans on the rate and quality of superficial healing.

Compared with the control experiments, the adhesion of the vehicle is accelerated in the case of the wounds treated with functionalized dextrans.

The re-epithelialization follows kinetics comparable to those observed under the action of FGFs.

The ratio P/A, where P is the perimeter of the wound and A the area of the scar, represents a totally significant decrease in the degree of scar retraction. The results obtained are illustrated in Table VI.

These experiments confirm the specific role of functionalized dextrans in the inhibition of scar retraction and deformation of the surrounding area of skin, as already specified above in Example D.

B—Histological Study

The analysis is identical to that performed in the previous Example.

It reveals, compared with the observations of the control experiments, a more rapid and more intense colonization of the collagen impregnated with functionalized dextrans from the various types of cells surrounding the wound.

The neoangiogenesis is distinct but less sustained than that observed in the presence of FGFs.

The extensions of the epidermis join up edge to edge at around day 4, which is at least 24 hours ahead of the re-epithelialization observed in the controls.

It is therefore apparent that there is a healing effect inherent in the action of functionalized dextrans which manifests itself as healing at the harmonious contours, resulting in a decrease in the natural contraction of the sides of the wound and an increased and rapid mobilization of cells colonizing the collagens, culminating in a denser and more vascularized regenerating tissue than that observed in the case of the control experiments. Such an effect might perhaps be explained by the fact that substituted functionalized dextrans potentiate, on the tissues, the action of FGFs secreted in situ by the surrounding tissues.

TABLE VI

The degrees of retraction P/A are shown for the collagen controls by themselves, collagen impregnated with type A dextran and the various dextrans listed above. All these molecules act at a dilution of 3 μg/ml

| P/A | 2 d | 4 d | 8 d |
|---|---|---|---|
| T(1) | 0.21 | 0.20 | 0.61 |
| T(2) | 0.20 | 0.25 | 0.55 |
| B | 0.16 | 0.18 | 0.30 |
| C | 0.15 | 0.18 | 0.26 |
| D | 0.13 | 0.13 | 0.20 |
| E | 0.14 | 0.16 | 0.22 |
| F | 0.10 | 0.11 | 0.20 |
| G | 0.15 | 0.18 | 0.29 |
| H | 0.13 | 0.14 | 0.30 |
| A + D | 0.18 | 0.20 | 0.28 |
| D + H | 0.11 | 0.15 | 0.22 |

(1): collagen
(2): collagen + A

As is apparent from the foregoing description, the invention is in no way limited to those modes of execution, embodiments and modes of application which have now been described more explicitly; on the contrary, it encompasses all the variants thereof which may occur to those skilled in the art, without deviating from the framework or the scope of the present invention.

We claim:

1. A method for regenerating cells and tissues in a patient in need thereof, wherein said cells and tissues are selected from skin and corneal cells and tissues, consisting essentially of administering to said patient an effective amount of at least one functionalized dextran in which each free reactive hydroxyl group of the dextran has been substituted with at least one group selected from the group consisting of carboxymethyl, benzylamide and benzylamide sulfonate, said at least one group present in said functionalized dextran in the following proportions:

carboxymethyl, between 42 and 89%;

benzylamide, between 0 and 24%;

benzylamide sulfonate, between 0 and 14%;

with the proviso that said functionalized dextran always includes in addition to carboxymethyl another group selected from the group consisting of benzylamide and benzylamide sulfonate.

* * * * *